US00PP36329P2

(12) United States Plant Patent
Boeder

(10) Patent No.: US PP36,329 P2
(45) Date of Patent: Dec. 17, 2024

(54) ***LAVANDULA* PLANT NAMED 'ZANLACUB'**

(50) Latin Name: *Lavandula angustifolia*
Varietal Denomination: ZANLACUB

(71) Applicant: Van Zanten Breeding B.V., Rijsenhout (NL)

(72) Inventor: Mark Roland Boeder, The Hague (NL)

(73) Assignee: Van Zanten Breeding B.V. (NL)

( * ) Notice: Subject to any disclaimer, the term of this patent is extended or adjusted under 35 U.S.C. 154(b) by 0 days.

(21) Appl. No.: 18/630,869

(22) Filed: Apr. 9, 2024

(51) Int. Cl.
*A01H 5/02* (2018.01)
*A01H 6/50* (2018.01)

(52) U.S. Cl.
USPC ..... Plt./445

(58) Field of Classification Search
USPC ..... Plt./445
See application file for complete search history.

*Primary Examiner* — Susan McCormick Ewoldt
*Assistant Examiner* — Zachariah Allan Kay
(74) *Attorney, Agent, or Firm* — Cassandra Bright

(57) ABSTRACT

A new and distinct cultivar of *Lavandula* plant named 'ZANLACUB' is disclosed, characterized by large flower spikes, white flowers, grey-green foliage, and vigorous growth. The new variety is a *Lavandula,* normally used for outdoor ornamental purposes.

4 Drawing Sheets

Latin name of the genus and species: *Lavandula angustifolia.*

Variety denomination: 'ZANLACUB'.

BACKGROUND OF THE INVENTION

The new *Lavandula* cultivar is a product of a planned breeding program conducted by the inventor at a nursery in De Lier, the Netherlands. The crossing resulting in this new variety was made during 2012.

The seed parent is an unpatented, proprietary *Lavandula* seedling. The pollen parent is a different unpatented, proprietary *Lavandula* seedling. The new variety was selected in 2015 by the inventor in a group of seedlings resulting from the 2012 crossing, at the same nursery in De Lier, the Netherlands.

Asexual reproduction of the new cultivar was performed by softwood cuttings. This was first performed at the same nursery in De Lier, the Netherlands in 2015, and has shown that the unique features of this cultivar are stable and reproduced true to type in multiple successive generations.

SUMMARY OF THE INVENTION

The cultivar 'ZANLACUB' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ZANLACUB' These characteristics in combination distinguish 'ZANLACUB' as a new and distinct *Lavandula* cultivar:

1. Large flower spikes.
2. Vigorous growth.

3. Grey-green foliage.
4. White flowers.

PARENT COMPARISONS

Plants of the new cultivar 'ZANLACUB' are similar to plants of the seed parent in most horticultural characteristics; however, plants of the new cultivar 'ZANLACUB' differ in the following:

1. Flower spikes of the new variety are larger than flower spikes of the seed parent.

Plants of the new cultivar 'ZANLACUB' are similar to plants of the pollen parent in most horticultural characteristics; however, plants of the new cultivar 'ZANLACUB' differ in the following;

1. Flowers of the new variety are white; flowers of the pollen parent are lavender.

COMMERCIAL COMPARISONS

Plants of the new cultivar 'ZANLACUB' are comparable to the commercial variety *Lavandula* 'Armtipp01', U.S. Plant Pat. No. 24,827. The two *Lavandula* varieties are similar in most horticultural characteristics; however, the new variety 'ZANLACUB' differs in the following:

1. Flowers of the new variety are white; flowers of this comparator are lavender.

Plants of the new cultivar 'ZANLACUB' are comparable to the commercial variety *Lavandula* 'Hidcote White', unpatented. The two *Lavandula* varieties are similar in most horticultural characteristics; however, the new variety 'ZANLACUB' differs in the following:

1. Growth habit of the new variety is more vigorous than the growth habit of this comparator.
2. Flowers of the new variety are larger than flowers of this comparator.

BRIEF DESCRIPTION OF THE PHOTOGRAPHS

The accompanying photograph in FIG. 1 illustrates in full color a typical plant of 'ZANLACUB' grown outdoors in De Lier, the Netherlands during June. Age of the plant photographed is approximately 2 years old from a rooted cutting.

Figure 1:
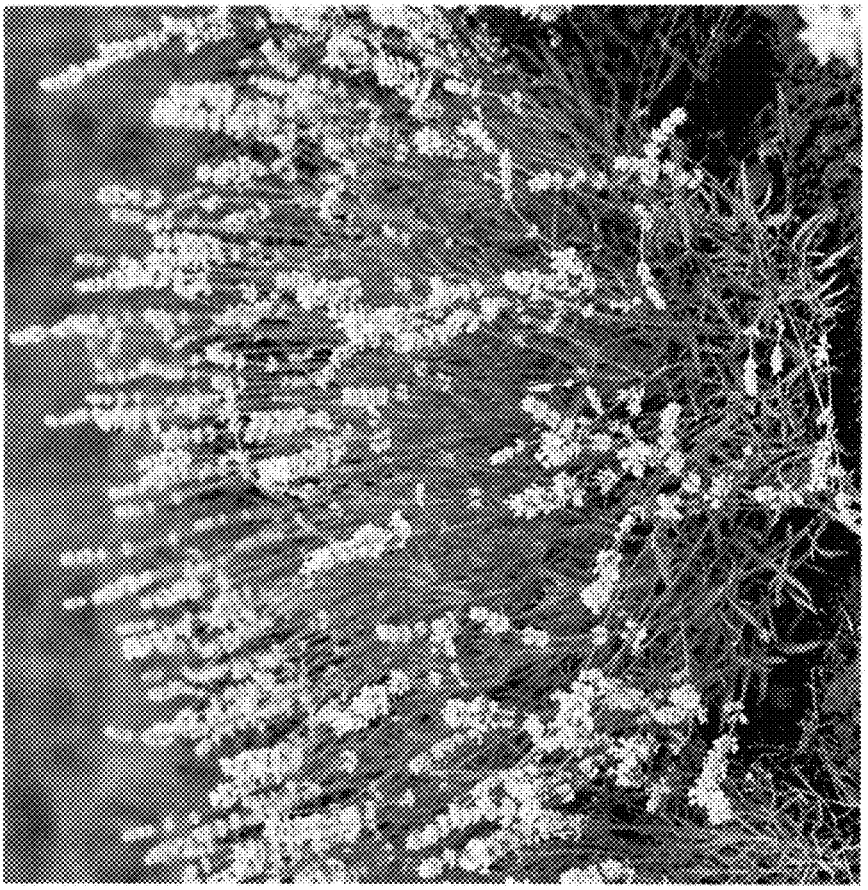
Figure 2:
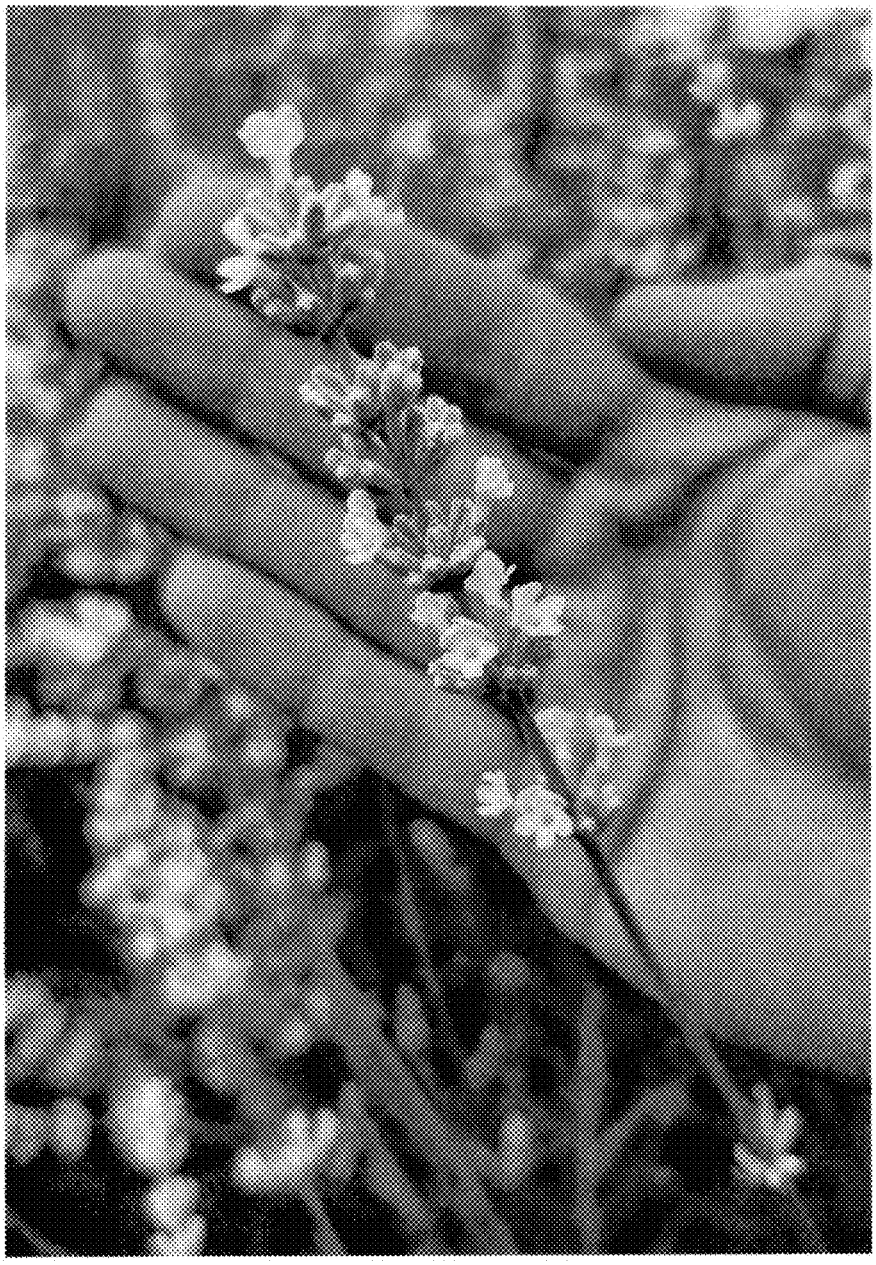
FIG. 2 illustrates a close up view of the inflorescence.
Figure 3:
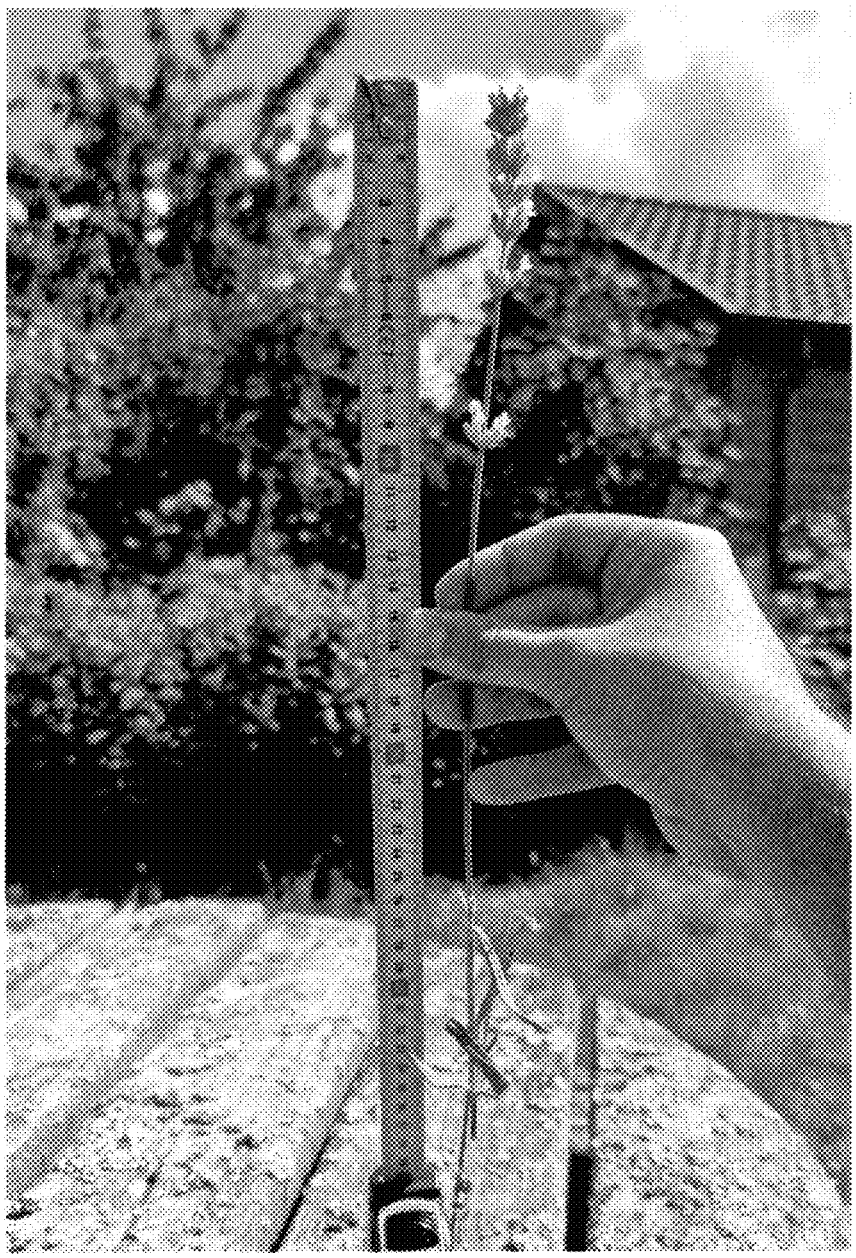
FIG. 3 illustrates a close up of a typical inflorescence, with measurements in centimeter adjacent.
Figure 4:
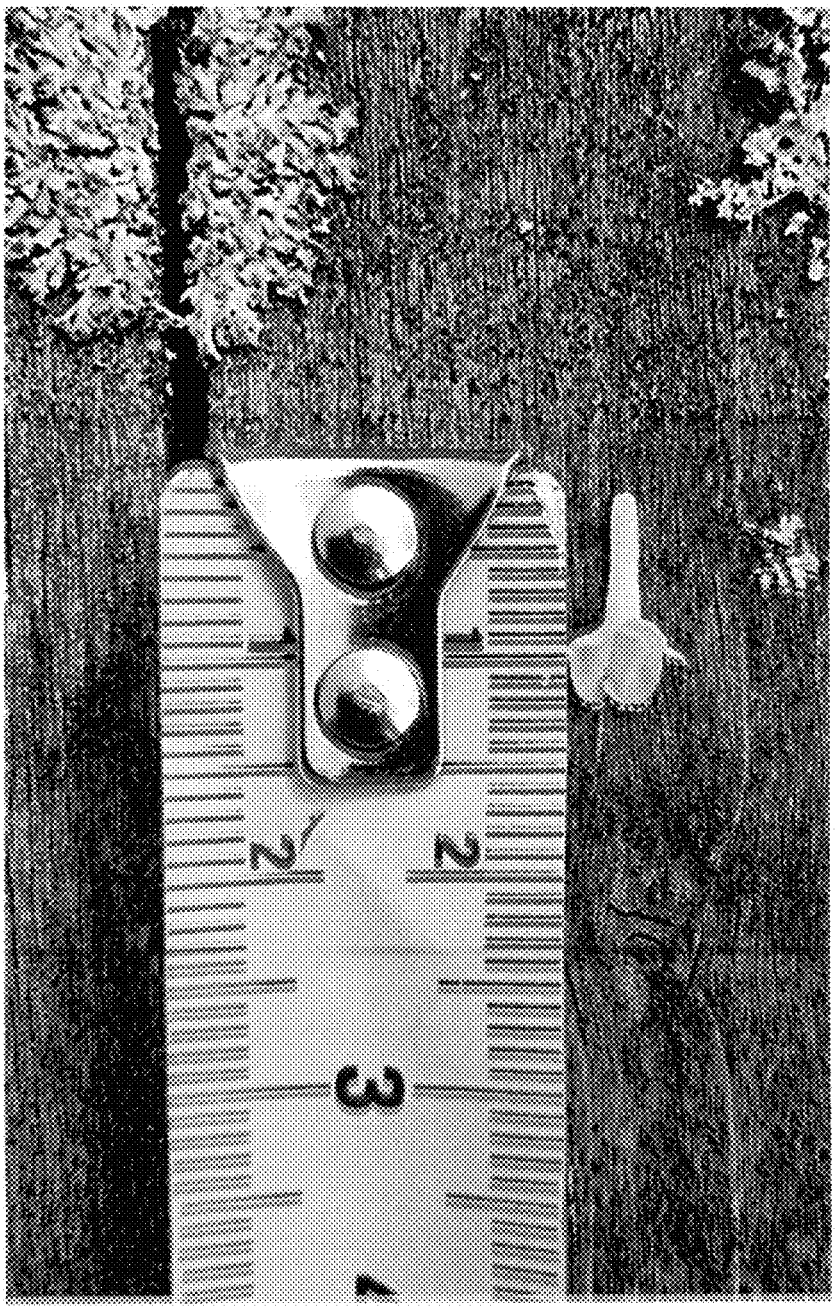
FIG. 4 illustrates a close up of a typical floret, with measurements in centimeter adjacent.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'ZANLACUB' plants grown outdoors in De Lier, the Netherlands. The growing temperature ranged from approximately 18° C. to 27° C. during the day and from approximately 5° C. to 10° C. during the night. General light conditions are normal sunlight and numerical values represent averages of typical plant types.

Botanical classification: *Lavandula angustifolia* 'ZANLACUB'

PROPAGATION

Type of propagation typically used: Cuttings.
Time to initiate roots:
Time to produce a rooted cutting:
Root description: Fine, fibrous.

PLANT

Age of plant described: 2 years old.
Plant type: Herbaceous perennial.
Growth habit: Upright, bushy.
Plant spread: 40 cm.
Plant height: 45 cm.
Growth rate: Vigorous.
Branching habit: Basal.
Length of primary lateral branches: 34 cm.
Diameter of lateral branches: 3 mm.
Stem:
- *Color*.—Young stems: RHS Green 137C. Mature stems: RHS Brown 201B.
- *Shape*.—Quadrangular.
- *Strength*.—Strong.

Internode length: 1.5 cm.

FOLIAGE

Leaf:
- *Arrangement*.—Opposite.
- *Attachment*.—Sessile.
- *Division*.—Simple.
- *Quantity*.—10 to 12 per flowering branch.
- *Length*.—5.5 cm.
- *Width*.—6 mm.
- *Shape*.—Narrowly oblong to narrowly oblanceolate.
- *Apex*.—Acute.
- *Base*.—Cuneate.
- *Margin*.—Entire.
- *Texture*.—Pubescent.
- *Fragrance*.—Strong.
- *Color*.—Young foliage upper side: RHS Grey-Green 191A. Young foliage under side: RHS Grey-Green 194A to 194B. Mature foliage upper side: Near RHS Green 137B. Mature foliage under side: Near RHS Green 138A.
- *Venation*.—Pattern: Pinnate. Venation color upper side: RHS Green 137B. Venation color under side: RHS Green 138B.

FLOWER

Natural flowering season: Early to late summer.

Inflorescence:
- *Type*.—Terminal.
- *Length*.—9.5 cm.
- *Width*.—1.5 cm.
- *Quantity*.—About 70.

Individual flowers:
- *Shape*.—Salverform.
- *Quantity*.—60 to 70 per inflorescence.
- *Diameter*.—8 mm.
- *Length*.—1.1 cm.
- *Persistence*.—Self-cleaning.
- *Fragrance*.—None.

Petals:
- *Arrangement*.—Tube, flared at end.
- *Number*.—4.
- *Shape*.—Spatulate.
- *Margin*.—Entire.
- *Apex*.—Upper petal split in two lobes, lower petal split in three lobes. Lobe tips rounded.
- *Base*.—Fused.
- *Length*.—Upper lip: 13 mm. Lower lips: 3 mm.
- *Width*.—Upper lip: 4 mm. Lower lips: 12 mm.
- *Texture*.—Glabrous.
- *Color*.—RHS White N155D.

Bud:
- *Shape*.—Elliptic to oblong.
- *Length*.—7 mm.
- *Diameter*.—2 mm.
- *Color*.—RHS Green 137C to 137D, with many wooly, white hairs.

Sepals:
- *Arrangement*.—Rotate, fused.
- *Shape*.—Linear, fused.
- *Apex*.—Broad acute.
- *Base*.—Fused.
- *Margin*.—Entire.
- *Quantity*.—5 per flower.
- *Length*.—7 mm.
- *Width*.—2 mm.
- *Texture*.—Pubescent.
- *Color*.—RHS Green 137C to 137D.

Calyx:
- *Shape*.—Campanulate.
- *Length*.—7 mm.
- *Width*.—2 mm.

Peduncle:
- *Length*.—24 cm.
- *Width*.—3 mm.
- *Texture*.—Pubescent.
- *Color*.—RHS Green 138B.
- *Strength*.—Flexible and moderately strong.

Pedicel:
*Length*.—1 mm.
*Diameter*.—1 mm.
*Color*.—RHS Green 138B.

Bracts:
*Shape*.—Rhomboidal.
*Apex*.—Cuspidate.
*Base*.—Cuneate.
*Margin*.—Entire.
*Color*.—RHS Green 138B.

REPRODUCTIVE ORGANS

Gynoecium:
*Pistil length*.—7 mm.
*Stigma shape*.—Narrow, club-shaped.
*Stigma color*.—RHS White 155A.
*Style length*.—6 mm.
*Ovary color*.—RHS Yellow-Green 146A.

Androecium:
*Stamen number*.—4.
*Filament length*.—1 mm.
*Filament color*.—RHS White NN155D.
*Anther length*.—0.5 mm.
*Anther shape*.—Dorsifixed.
*Anther color*.—RHS Grey-Green 197A to 197B.
*Pollen color*.—RHS Yellow 23A.

OTHER CHARACTERISTICS

Fruits and seeds: Not observed to date.
Disease/pest resistance: Typical resistance and susceptibility to normal diseases and pests of *Lavandula* observed.
Temperature range: USDA zone 7b.

What is claimed is:

1. A new and distinct cultivar of *Lavandula* plant named 'ZANLACUB' as herein illustrated and described.

* * * * *